US010856772B2

(12) United States Patent
Naito et al.

(10) Patent No.: US 10,856,772 B2
(45) Date of Patent: Dec. 8, 2020

(54) CALCULATION DEVICE, CALCULATION METHOD, AND NON-TRANSITORY COMPUTER READABLE RECORDING MEDIUM

(71) Applicant: OMRON Corporation, Kyoto (JP)

(72) Inventors: Sayaka Naito, Joyo (JP); Yoshikazu Mori, Koriyama (JP); Kazuki Kasai, Tokyo (JP)

(73) Assignee: OMRON Corporation, Kyoto (JP)

( * ) Notice: Subject to any disclaimer, the term of this patent is extended or adjusted under 35 U.S.C. 154(b) by 315 days.

(21) Appl. No.: 15/751,479

(22) PCT Filed: Jan. 6, 2017

(86) PCT No.: PCT/JP2017/000325
§ 371 (c)(1),
(2) Date: Feb. 9, 2018

(87) PCT Pub. No.: WO2017/141565
PCT Pub. Date: Aug. 24, 2017

(65) Prior Publication Data
US 2018/0235515 A1 Aug. 23, 2018

(30) Foreign Application Priority Data
Feb. 15, 2016 (JP) .................. 2016-025958

(51) Int. Cl.
*A61B 5/107* (2006.01)
*G01B 21/06* (2006.01)
(Continued)

(52) U.S. Cl.
CPC .......... *A61B 5/1072* (2013.01); *A61B 5/1121* (2013.01); *G01B 21/06* (2013.01);
(Continued)

(58) Field of Classification Search
CPC .................................................. A61B 5/1072
(Continued)

(56) References Cited

U.S. PATENT DOCUMENTS 7,611,520 B2 * 11/2009 Broers ................... A61B 5/103
33/512
2006/0195223 A1 * 8/2006 Kawai .................. B62D 57/032
700/245
(Continued)

FOREIGN PATENT DOCUMENTS

CN     1996205      7/2007
CN     101546196    9/2009
(Continued)

OTHER PUBLICATIONS

"International Search Report (Form PCT/ISA/210) of PCT/JP2017/000325," dated Mar. 28, 2017, with English translation thereof, pp. 1-4.
(Continued)

*Primary Examiner* — Ricky Ngon
(74) *Attorney, Agent, or Firm* — JCIPRNET

(57) ABSTRACT

A calculation device, a calculation method, and a non-transitory computer readable recording medium including a calculation program with which a length of a target region required for a body model can be determined by means of a simple motion are provided. This calculation device configures a wearable device to initiate measurement of a measurement target region. After the measurement of the measurement target region is initiated, a worker wearing the wearable device performs a motion such as rotation of an arm, for example, etc. The calculation device acquires measured information two or more times over time and calculates a body model on the basis of the acquired measured information. During calculation of the body model, calculation is performed to determine a length of a calcu-
(Continued)

lation target region by approximately determining a circle or sphere having the length from the rotation center to the calculation target region as a radius using a mathematical method such as a least-squares method on the basis of the measured information acquired over time. Then, the calculation device records the calculated body model in a body model recording unit.

11 Claims, 6 Drawing Sheets

(51) Int. Cl.
  *G06K 9/00* (2006.01)
  *G06F 3/01* (2006.01)
  *G06T 17/00* (2006.01)
  *A61B 5/11* (2006.01)
(52) U.S. Cl.
  CPC .......... *G06F 3/011* (2013.01); *G06K 9/00342* (2013.01); *G06K 9/00369* (2013.01); *G06T 17/00* (2013.01); *A61B 2503/20* (2013.01)
(58) Field of Classification Search
  USPC ......................................................... 702/127
  See application file for complete search history.

(56) References Cited

U.S. PATENT DOCUMENTS

| | | | |
|---|---|---|---|
| 2008/0115562 A1 | 5/2008 | Haino et al. | |
| 2016/0022173 A1* | 1/2016 | Schubert | A61B 5/1072 600/587 |
| 2016/0331276 A1* | 11/2016 | Shoshan | A61B 5/6898 |
| 2016/0345868 A1* | 12/2016 | Rost | A61B 5/1072 |
| 2017/0215766 A1* | 8/2017 | Fernandez Prada | A61B 5/1072 |

FOREIGN PATENT DOCUMENTS

| | | |
|---|---|---|
| CN | 103197674 | 7/2013 |
| CN | 103546605 | 1/2014 |
| CN | 103706108 | 4/2014 |
| CN | 104339352 | 2/2015 |
| JP | 2000291748 | 10/2000 |
| JP | 2010-014712 | 1/2010 |
| JP | 2013-027629 | 2/2013 |
| JP | 2014-025857 | 2/2014 |
| JP | 2016-206081 | 12/2016 |
| JP | 2017-038821 | 2/2017 |

OTHER PUBLICATIONS

"Written Opinion of the International Searching Authority (Form PCT/ISA/237) of PCT/JP2017/000325," dated Mar. 28, 2017, with English translation thereof, pp. 1-8.

"Office Action of China Counterpart Application," with English translation thereof, dated Nov. 19, 2019, p. 1-p. 12.

M. Sajeewani Karunarathne et al., "A machine-driven process for human limb length estimation using inertial sensors, " 2015 IEEE 10th International Conference on Industrial and Information Systems (ICIIS), Dec. 18-20, 2015, pp. 1-5.

Yan Wang et al., "A simple calibration for upper limb motion tracking and reconstruction, " 2014 36th Annual International Conference of the IEEE Engineering in Medicine and Biology Society, Aug. 26-30, 2014, pp. 1-4.

"Search Report of Europe Counterpart Application", dated Aug. 27, 2019, p. 1-p.8.

Office Action of China Counterpart Application, with English translation thereof, dated Jun. 12, 2019, pp. 1-14.

* cited by examiner

CALCULATION DEVICE, CALCULATION METHOD, AND NON-TRANSITORY COMPUTER READABLE RECORDING MEDIUM

CROSS-REFERENCE TO RELATED APPLICATION

This application is a 371 application of the International PCT application serial no. PCT/JP2017/000325, filed on Jan. 6, 2017, which claims the priority benefit of Japan application no. 2016-025958, filed on Feb. 15, 2016. The entirety of each of the above-mentioned patent applications is hereby incorporated by reference herein and made a part of this specification.

TECHNICAL FIELD

The present invention relates to a calculation device that calculates a length of a calculation target region of a human body on the basis of results of measuring a measurement target region of the human body, a calculation method using this calculation device, and a non-transitory computer readable recording medium including a calculation program for realizing this calculation device.

BACKGROUND ART

In various workplaces such as a factory, a machine such as an industrial robot and a person carry out work in cooperation with each other. Due to the intention for the person to safely carry out cooperative work with the machine, a technique such as motion sensing for detecting a motion of the person using a sensor is attracting attention.

For example, when motion sensing of the person is performed using an inertial sensor, information indicating a shape of the body of a person to be measured is pre-recorded as a body model obtained by modeling the shape of the human body. When the person to be measured conducts a motion, the motion of the person to be measured is calculated on the basis of a result of measuring the body using the same inertial sensor and the pre-recorded body model. For example, an exercise guidance device that analyzes suitable motions of a body model on the basis of a pre-stored body model is disclosed in Patent Literature 1. In Patent Literature 1, in order to measure a motion using a sensor, a person to be measured wears a sensor module.

CITATION LIST

Patent Literature

[Patent Literature 1]
Japanese Patent Application Laid-Open No. 2013-27629

SUMMARY OF INVENTION

Technical Problem

However, in order to perform sensing corresponding to a pre-recorded body model, a sensor must be mounted at a position that conforms to the recorded body model, but it is difficult to adjust the mounting position in accordance with a somatotype. If the sensor module is mounted before work, information becoming the body model is acquired at all times, and the body model is calculated and recorded, a requirement of the complicated motion leads to a reduction in workability. Further, when it comes to using an established body model without adjusting the mounting position and acquiring information about a previous body model, precision of a calculation of the motion is reduced. In Patent Literature 1, a technique for previously acquiring this body model is not sufficiently disclosed.

The present invention was made in view of such circumstances, and a main object thereof is to provide a calculation device capable of finding a length of a target region with a relatively simple motion.

Another object of the present invention is to provide a calculation method using the calculation device according to the present invention.

Still another object of the present invention is to provide a non-transitory computer readable recording medium including a calculation program for realizing the calculation device according to the present invention.

Solution to Problem

To solve the above problems, a calculation device set forth herein is a calculation device that calculates a length of a calculation target region of a human body on the basis of results of measuring a measurement target region of the human body, and includes: a state information acquisition unit configured to acquire state information that indicates a position or the position and a state of a posture of the measurement target region of the human body on the basis of measured results; and a calculation unit configured to calculate a length using a region from a rotation center in a motion of the human body to the measurement target region as the calculation target region on the basis of the state information acquired by the state information acquisition unit.

In the calculation device, the calculation unit includes: a unit configured to calculate a length using a region from a first rotation center to the measurement target region as a first calculation target region; a unit configured to calculate a length using a region from a second rotation center between the first rotation center and the measurement target region to the measurement target region as a second calculation target region; and a unit configured to calculate a length using a region from the first rotation center to the second rotation center as a third calculation target region on the basis of a difference between the length of the first calculation target region and the length of the second calculation target region.

In the calculation device, the calculation unit calculates the length of the calculation target region on the basis of the state information by approximately obtaining a circle or a sphere having a length from the rotation center to the calculation target region as a radius thereof.

In the calculation device, the calculation unit calculates the length of the calculation target region by a least-squares method on the basis of the state information indicating the position of the measurement target region.

In the calculation device, the rotation center is a joint.

In the calculation device, the calculation unit generates a body model relevant to a shape of the human body on the basis of a calculated result.

The calculation device further includes a measured information acquisition unit configured to acquire at least one of a velocity, an acceleration, an angular velocity, an angular acceleration, a pressure, and a magnetism, which are results of measuring the measurement target region of the human body, as measured information. The state information acquisition unit calculates and acquires the state information about the measurement target region of the human body on the basis of measured information acquired by the measured information acquisition unit.

Further, a calculation method set forth herein is a calculation method for calculating a length of a calculation target region of a human body on the basis of results of measuring a measurement target region of the human body, and includes: a step of a state information acquisition unit acquiring state information that indicates a position or the position and a state of a posture of the measurement target region of the human body on the basis of measured results; and a step of a calculation unit calculating a length using a region from a rotation center in a motion of the human body to the measurement target region as the calculation target region on the basis of the state information acquired by the state information acquisition unit.

Further, a calculation program set forth herein is a calculation program that causes a computer to calculate a length of a calculation target region of a human body on the basis of measured information obtained by measuring a measurement target region of the human body, the calculation program causing the computer to perform: a step of acquiring state information that indicates a position or the position and a state of a posture of the measurement target region of the human body on the basis of measured results; and a step of calculating a length using a region from a rotation center in a motion of the human body to the measurement target region as the calculation target region on the basis of the acquired state information.

The calculation device, the calculation method, and the calculation program which are set forth herein calculate the length using the region from the rotation center in the motion of the human body to the measurement target region as the calculation target region on the basis of the results of measuring the measurement target region.

Advantageous Effects of Invention

The present invention measures a measurement target region of a human body and calculates a length using a region from a rotation center in a motion of the human body to the measurement target region as a calculation target on the basis of results of measuring the measurement target region. Thereby, since a motion of the human body can approximate a motion such as a circular motion and a length of the calculation target can be calculated as a radius of the motion, an excellent effect of making it possible to calculate a calculation target usable as, for instance, a body model only by a person to be measured performing a simple motion is achieved.

DESCRIPTION OF EMBODIMENTS

Hereinafter, an embodiment of the present invention will be described with reference to the drawings. The following embodiment is an example in which the present invention is embodied, and does not limit a technical scope of the present invention by nature.

<Outline>

Figure 1:
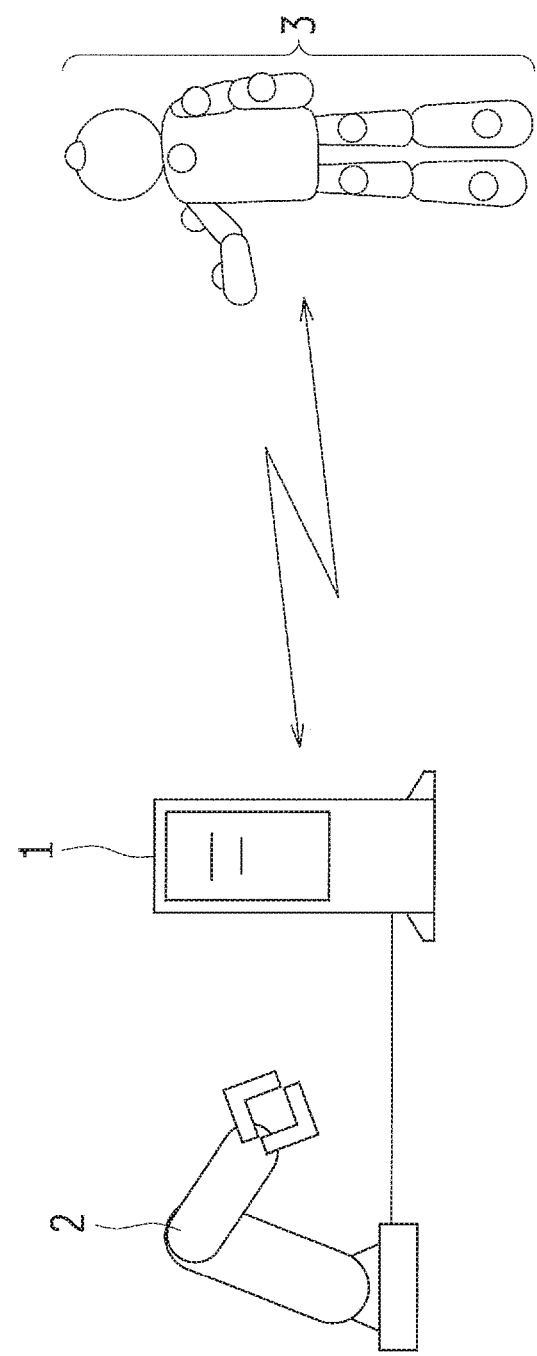
FIG. 1 is an explanatory diagram conceptually illustrating an example of a system using a calculation device set forth herein.

First, an outline of a system using a calculation device set forth herein will be described. FIG. 1 is an explanatory diagram conceptually illustrating an example of a system using a calculation device 1 set forth herein. The calculation device 1 set forth herein is used to calculate a body model relevant to a worker, for instance, in a system such as a factory automation (FA) system in which the worker does work in cooperation with a robot 2 which is a working robot (hereinafter referred to as a robot) 2 that does work according to a predetermined control instruction. The worker wears a wearable device 3 having various inertial sensors such as an acceleration sensor, a gyroscope sensor, and the like on various measurement target regions of a body such as the head, an upper arm, a forearm, the chest, the abdomen, a thigh, a lower leg, and the like. The wearable device 3 having various inertial sensors measures the measurement target regions of the body of the target person and outputs various kinds of measured information indicating the measured results. As the sensors mounted on the wearable device 3, in addition to the inertial sensors such as the acceleration sensor, the gyroscope sensor, and the like, sensors such as a magnetic sensor, a pressure sensor, and the like may be used. In FIG. 1, to facilitate understanding, regions at which the inertial sensors are located are shown with white circles on the worker wearing the wearable device 3.

The calculation device 1 supports coordination work between the worker and the robot 2 through a technique such as motion sensing that acquires various kinds of information output from the wearable device 3 and the robot 2 and detects a motion of the worker. In the event of the motion sensing, a body model obtained by previously modeling a shape of the worker is required. The calculation device 1 acquires measured information, which is obtained by measuring the measurement target regions, from the wearable device 3, which the worker wears, calculates calculation target regions of the worker required for construction of the body model, and calculates shape information, which is information for the body model. The calculation device 1 is configured using a computer such as a control computer for controlling the robot 2, is connected with the wearable device 3 and the robot 2 to enable communication therewith through a radio or wired communication method, and performs communication of various information and signals. The calculation device 1 may be designed to be separated from the wearable device 3 and the robot 2 and perform calculation of the body model (to be described below) off line.

<Device configuration>

Figure 2:
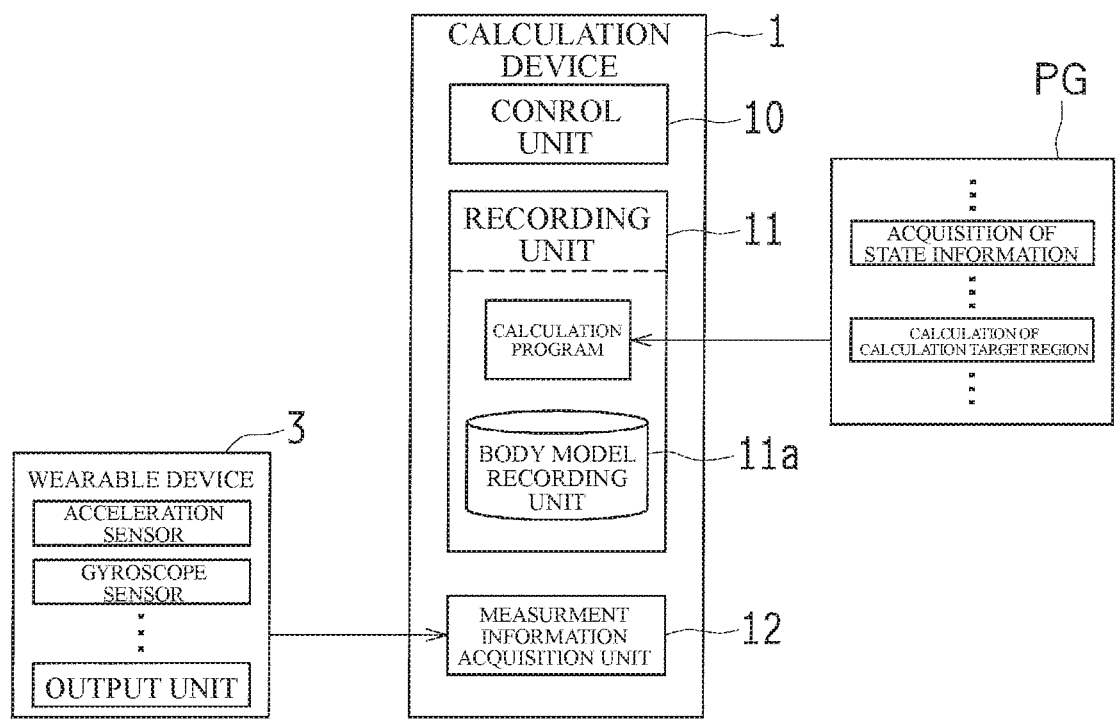
FIG. 2 is a block diagram illustrating an example of hardware configurations of the calculation device and a wearable device set forth herein.

Next, configurations of the various devices set forth herein will be described mainly on the basis of the calculation device 1. FIG. 2 is a block diagram illustrating an example of hardware configurations of the calculation device 1 and the wearable device 3 set forth herein. The calculation device 1 includes a control unit 10 and a recording unit 11. The calculation device 1 further includes a measured information acquisition unit 12 as an interface with the wearable device 3.

The control unit 10 is configured using a processor such as a central processing unit (CPU) and a memory such as a register, controls the entire device by executing various instructions, and outputs a control instruction to the robot 2.

The recording unit 11 includes a non-volatile memory such as a read-only memory (ROM), an erasable programmable read-only memory (EPROM), or the like, a volatile memory such as a random access memory (RAM), and a recording medium such as a hard disc drive, a semiconductor memory, or the like, and records data such as various programs and information. A calculation program PG making a computer such as a control computer function as the calculation device 1 according to the present invention is recorded in a recording region of the recording unit 11.

Further, a part of the recording region of the recording unit 11 is used as a database of a body model recording unit 11a or the like that records a body model modeling a shape of the body of the worker. The body model is a numerical model that is modeled using numerical values such as lengths of various regions such as an upper arm, a forearm, a thigh, a lower leg, and the like. Body models relevant to a plurality of workers are recorded in the body model recording unit 11a in association with worker specific information (worker IDs) which specify the workers. Without using the part of the recording region of the recording unit 11 constituting the calculation device 1 as the body model recording unit 11a, a recording device such as a server computer or the like that records various kinds of information may be connected to the calculation device 1, and a part of a recording region of the recording device connected to the calculation device 1 may be used as the database of the body model recording unit 11a or the like. That is, the database of the body model recording unit 11a or the like can be designed through various modes as long as it is accessible by the control unit 10 constituting the calculation device 1 and is maintained to be recordable and readable.

The measured information acquisition unit 12 is an interface that acquires various kinds of information such as measured information or the like, which indicates the measured results, from the wearable device 3.

The computer such as the control computer or the like reads the various programs, for instance the calculation program PG, recorded in the recording unit 11 and executes various steps such as acquiring state information included in the read calculation program PG, calculating a calculation target region on the basis of the state information, and the like under the control of the control unit 10, and thereby functions as the calculation device 1.

The wearable device 3 includes various configurations including a measurement unit using sensors such as an acceleration sensor, a gyroscope sensor, and the like for detecting information about motions, and an output unit and the like other than the measurement unit. As the sensors mounted on the wearable device 3, in addition to the acceleration sensor and the gyroscope sensor, various sensors such as a magnetic sensor, a pressure sensor, and the like can be used. The wearable device 3 measures a physical quantity such as a velocity, an angular velocity, an acceleration, an angular acceleration, a pressure, a magnetism, and the like using the measurement unit and outputs the measured results from the output unit to the calculation device 1 as measured information such as raw data that indicates the measured results relevant to the motions of the worker. The calculation device 1 acquires the measured information indicating the physical quantity such as the velocity, the angular velocity, the acceleration, the angular acceleration, the pressure, the magnetism, and the like through the measured information acquisition unit 12, and acquires state information such as position information, posture information, and the like indicating states of the measurement target region on the basis of the acquired measured information. For example, the acceleration measured by the acceleration sensor is integrated twice so that the position information can be calculated. The calculation of the state information such as the position information, the posture information, and the like based on the measured information indicating the physical quantity such as the velocity, the angular velocity, the acceleration, the angular acceleration, the pressure, the magnetism, and the like may be configured to be calculated by either the wearable device 3 or the calculation device 1.

Figure 3:
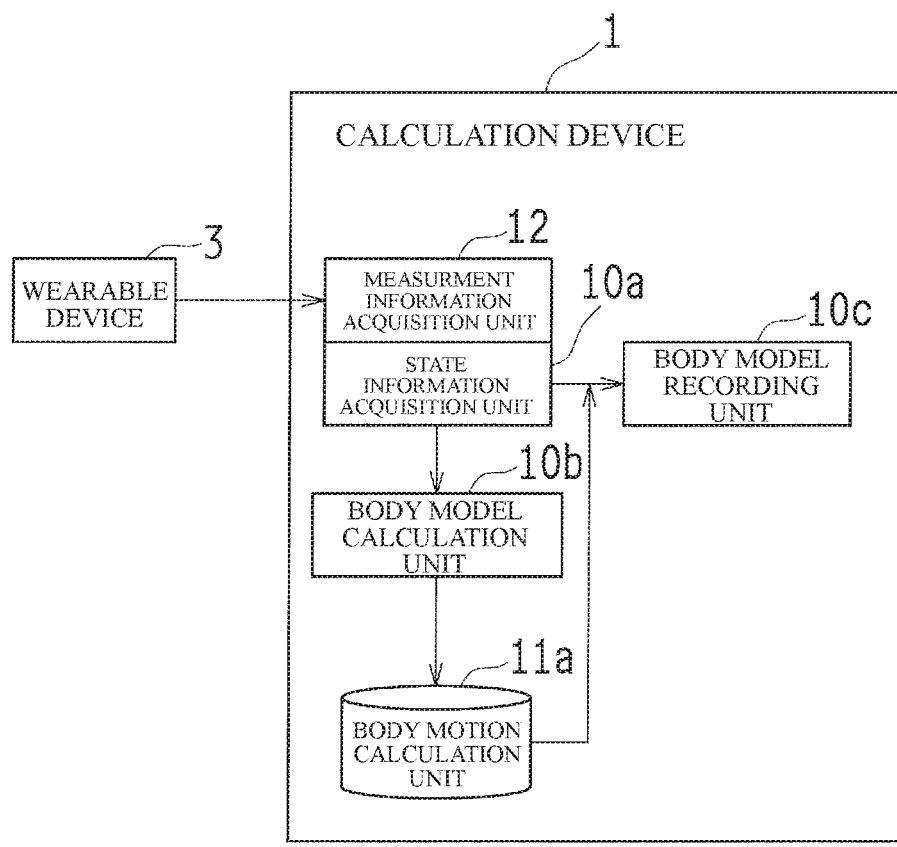
FIG. 3 is a functional block diagram illustrating an example of functional configurations of the calculation device and the wearable device set forth herein.

FIG. 3 is a functional block diagram illustrating an example of functional configurations of the calculation device 1 and the wearable device 3 set forth herein. The calculation device 1 executes various programs such as the calculation program PG, and thereby realizes functions to execute various calculations of a state information acquisition unit 10a, a body model calculation unit 10b, a body motion calculation unit 10c, and the like on the basis of the control of the control unit 10. The various calculation units that realize these various functions may be implemented by dedicated circuits using a semiconductor chip such as a large scale integration (LSI), a very large scale integration (VLSI), or the like.

The state information acquisition unit 10a obtains and acquires the state information such as the position information, the posture information, and the like of the measurement target region by calculating the state information on the basis of the measured information indicating the physical quantity, such as the velocity, the angular velocity, the acceleration, the angular acceleration, the pressure, the magnetism, and the like, which the measured information acquisition unit 12 acquires from the wearable device 3. When the wearable device 3 calculates the state information such as the position information, the posture information, and the like according to the measured information and the calculation device 1 acquires the state information, the state information acquisition unit 10a acquires the acquired state information acting as information used for the following calculation with no change.

The body model calculation unit 10b performs the calculation, which computes the body model obtained by modeling the shape of the body of the worker, on the basis of the various kinds of state information such as the position information, the posture information, and the like which the state information acquisition unit 10a acquires.

The body motion calculation unit 10c performs the calculation, which computes a motion state of the calculation target region of the body such as a hand, a foot, and the like of the worker, on the basis of the state information acquired by the state information acquisition unit 10a and the body model recorded in the body model recording unit 11a. The motion state is computed, for instance, as information about a position and a motion direction of the calculation target region, a prediction position and a prediction motion direction after a predetermined time and the like.

<Calculation>

Figure 4:
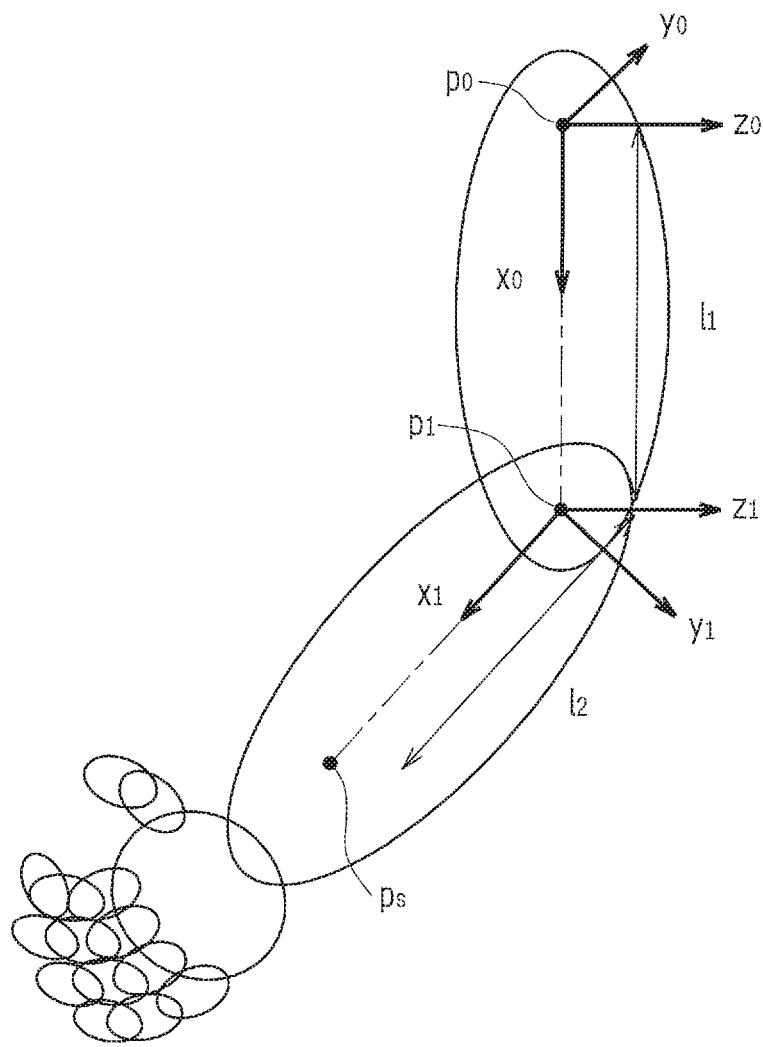
FIG. 4 is a conceptual diagram illustrating a part of a modeled human body in a calculation method using the calculation device set forth herein.

Next, a calculation method will be described. FIG. 4 is a conceptual diagram illustrating a part of a modeled human body in a calculation method using the calculation device 1 set forth herein. In the calculation method exemplified herein, a measurement target region of a worker is measured to acquire measured information over time, and a length of a radius of rotation from a position, which is the rotation center, to the measurement target region is set as a calculation target on the basis of state information calculated from the acquired measured information. The position, which is the rotation center, is a region such as a joint such as a shoulder joint, an elbow joint, a radiocarpal joint (a wrist), a hip joint, a knee joint, a talocrural joint (a malleolus), and the like, or a waist, a neck, and the like excluding a joint. A position, which is the measurement target region, is a region such as the head, an upper arm, a forearm, the chest, the abdomen, a thigh, a lower leg, and the like which correspond to the inertial sensors of the wearable device 3. In FIG. 4, an example in which the shoulder joint and the elbow joint are used as the rotation center and the vicinity of the wrist of the forearm is used as the measurement target region is illustrated.

In FIG. 4, a relative coordinate system of the upper arm using a shoulder joint $p_0$ as an origin is shown as $p_0$-$x_0y_0z_0$, and a relative coordinate system of the upper arm using an elbow joint $p_1$ as an origin is shown as $p_1x_1y_1z_1$. Each of the coordinate systems is an orthogonal coordinate system. Pieces of position information about the shoulder joint, the elbow joint, and the measurement target region relative to an origin of an absolute coordinate system taken as an option are shown as $p_0(x_{p0}, y_{p0}, z_{p0})$, $p_1(x_{p1}, y_{p1}, z_{p1})$, and $p_s(x_s, y_s, z_s)$. A length of the upper arm is shown as a length $l_1$ from the shoulder joint $p_0$ to the elbow joint $p_1$. A length from the elbow joint $p_1$ to a measurement target region $p_s$ close to the wrist is shown as a length $l_2$. When the position of the measurement target region is close to the wrist, the length $l_2$ approximates a length of the forearm. When a motion by which the arm is rotated by serving the shoulder as the rotation center is performed, a length $(l_1+l_2)$ from the shoulder joint $p_0$, which is the rotation center, to the measurement target region $p_s$ close to the wrist is a calculation target as a radius of rotation based on the state information calculated from the measured information of the measurement target region. When a motion by which the forearm is rotated by serving the elbow as the rotation center is performed, the length $l_2$ that is approximated to the forearm from the elbow joint $p_1$, which is the rotation center, to the measurement target region $p_s$ close to the wrist is the calculation target as the radius of rotation on the basis of the state information calculated from the measured information of the measurement target region. Further, a difference between the lengths, which are these calculated results, is calculated, and thereby the length $l_t$ of the upper arm shown from the shoulder joint $p_0$ to the elbow joint $p_1$ becomes the calculation target. Here, the motion is shown as the motion made to be rotated about the rotation center. However, it is not necessary to perform a single rotation, that is, a rotation of 360 degrees, and the motion may be a reciprocating motion within a predetermined angle, that is, an oscillating motion centered on the rotation center.

For the calculation method, various methods for setting the rotation center as $p(x, y, z)$ and approximately obtaining a circle or a sphere in which a length l of the calculation target up to the measurement target region $p_s(x_s, y_s, z_s)$ is set as a radius can be applied.

An example of the calculation method based on position information using a least-squares method will be described. First, as a sample, the worker fixes the rotation center such as the shoulder joint, the elbow joint, or the like and performs a motion for rotating the arm, the forearm, or the like, and measures the position of the measurement target region $p_s$ at a plurality of points (i=1,2,3, . . . ) over time during the motion. Thereby, the calculation device 1 can acquire position information $p_{si}(x_{si}, y_{si}, z_{si})$ of the plurality of points of the measurement target region $p_{si}$. Here, when the length, which is the calculation target, is defined as l, the rotating motion can approximate a three-dimensional circle or sphere, and thus the rotation center p, the measurement target region $p_s$ and the length l can approximate a relation of formula (1) below.

$$(x_{si}-x)^2+(y_{si}-y)^2+(z_{si}-z)^2=l^2 \quad (1)$$

wherein (x, y, z): coordinates of the rotation center p,
$(x_{si}, y_{si}, z_{si})$: position information of the measurement target region $p_{si}$, i=1, 2, 3, . . . , and
l: a length (the calculation target) from the rotation center p to the measurement target region $p_{si}$.

When an error is defined as e, the error e can be expressed with formula (2) below.

$$e=(x_{si}-x)^2+(y_{si}-y)^2+(z_{si}-z)^2-l^2 \quad (2)$$

wherein e: an error.
Here, when algebraic numbers A, B, C, and D are defined to be A=−2x, B=−2y, C=−2z, and D=$x^2+y^2+z^2-l^2$, formula (2) can be transformed to formula (3) below.

$$e=x^2+y^2+z^2+Ax+By+Cz+D \quad (3)$$

wherein A: −2x,
B: −2y,
C: −2z, and
D: x2+y2+z2−l2.
Further, when a square sum of the error e is defined as E, formula (4) below can be defined by the least-squares method.

$$E=\Sigma e^2=\Sigma(x^2+y^2+z^2+Ax+By+Cz+D)^2=0 \quad (4)$$

Here, when E is partially differentiated with respect to A, B, C, and D, a result is formulae (5) to (8) below.

$$\partial E/\partial A=0 \quad (5)$$

$$\partial E/\partial B=0 \quad (6)$$

$$\partial E/\partial C=0 \quad (7)$$

$$\partial E/\partial D=0 \quad (8)$$

When formulae (5) to (8) are expressed using a matrix and are solved with respect to A, B, C, and D, a result is obtained like formulae (9) and (10) below.

[Math. 1]

$$\begin{pmatrix} 2\Sigma x_{si}^2 & \Sigma x_{si}y_{si} & \Sigma x_{si}z_{si} & \Sigma x_{si} \\ \Sigma x_{si}y_{si} & 2\Sigma y_{si}^2 & \Sigma y_{si}z_{si} & \Sigma y_{si} \\ \Sigma x_{si}z_{si} & \Sigma y_{si}z_{si} & 2\Sigma z_{si}^2 & \Sigma z_{si} \\ \Sigma x_{si} & \Sigma y_{si} & \Sigma z_{si} & 2 \end{pmatrix} \begin{pmatrix} A \\ B \\ C \\ C \end{pmatrix} = \begin{pmatrix} -\Sigma(x_{si}^3+x_{si}y_{si}^2+x_{si}z_{si}^2) \\ -\Sigma(x_{si}^2y_{si}+y_{si}^3+y_{si}z_{si}^2) \\ -\Sigma(x_{si}^2z_{si}+y_{si}^2z_{si}+z_{si}^3) \\ -\Sigma(x_{si}^2+y_{si}^2+z_{si}^2) \end{pmatrix} \quad (9)$$

$$\begin{pmatrix} A \\ B \\ C \\ C \end{pmatrix} = \begin{pmatrix} 2\Sigma x_{si}^2 & \Sigma x_{si}y_{si} & \Sigma x_{si}z_{si} & \Sigma x_{si} \\ \Sigma x_{si}y_{si} & 2\Sigma y_{si}^2 & \Sigma y_{si}z_{si} & \Sigma y_{si} \\ \Sigma x_{si}z_{si} & \Sigma y_{si}z_{si} & 2\Sigma z_{si}^2 & \Sigma z_{si} \\ \Sigma x_{si} & \Sigma y_{si} & \Sigma z_{si} & 2 \end{pmatrix}^{-1} \begin{pmatrix} -\Sigma(x_{si}^3+x_{si}y_{si}^2+x_{si}z_{si}^2) \\ -\Sigma(x_{si}^2y_{si}+y_{si}^3+y_{si}z_{si}^2) \\ -\Sigma(x_{si}^2z_{si}+y_{si}^2z_{si}+z_{si}^3) \\ -\Sigma(x_{si}^2+y_{si}^2+z_{si}^2) \end{pmatrix} \quad (10)$$

The length l of the region, which is the calculation target, and coordinates (x, y, z) of the rotation center p as another calculation target can be computed from A, B, C, and D. When this calculation method is applied to compute the length $(l_1+l_2)$ from the shoulder joint $p_0$ to the measurement target region $p_s$ close to the wrist and coordinates $(x_{p0}, y_{p0}, z_{p0})$ of the shoulder joint $p_0$, the worker performs a motion of rotating his or her arm with the elbow straighten. The rotation center is calculated as the shoulder joint $p_0$ on the basis of the measured result of the measurement target region $p_s$ during the rotating motion, and thereby the length $(l_1+l_2)$ from the shoulder joint $p_0$ to the measurement target region $p_s$ close to the wrist and the coordinates $(x_{p0}, y_{p0}, z_{p0})$ of the shoulder joint $p_0$ can be computed. Likewise, the first worker performs a motion of rotating his or her forearm around the elbow, and calculates the rotation center as the elbow joint $p_l$ on the basis of the measured result of the measurement target region $p_s$ during the rotating motion, and thereby the length $l_2$ of the forearm from the elbow joint $p_1$ to the measurement target region $p_s$ close to the wrist and coordinates $(x_{p1}, y_{p1}, z_{p1})$ of the elbow joint $p_1$ can be computed. The length $l_2$ is subtracted from the length $(l_1+l_2)$, and thereby the length $l_1$ of the upper arm can be calculated.

The method for calculating the calculation target region such as the length of the arm from the state information based on the measured result of the calculation target region is not limited to the method for calculating the calculation target region from the position information, and various calculating methods can be applied thereto. For example, when the rotating motion around the rotation center $p(x, y, z)$ is performed like when the forearm is rotated using the elbow joint as the rotation center, the length l of the calculation target region such as the forearm and the coordinates $(x, y, z)$ of the rotation center p can be calculated by a relation between a velocity and an angular velocity.

That is, position information $(x_{si}, y_{si}, z_{si})$ and posture information $(\alpha_{si}, \beta_{si}, \gamma_{si})$, which are the state information based on the measured result of the measurement target region $p_{si}$, are first acquired at a plurality of points (i=1, 2, 3, . . . ) over time. When radious of rotation of x-axial, y-axial, and z-axial directions while the rotating motion is performed are defined as $r_x$, $r_y$, and $r_z$, differentiation of position information $(x_s, y_s, z_s)$ and posture information $(\alpha_s, \beta_s, \gamma_s)$ of the measurement target region $p_s$ can be expressed as formulae (11) to (13) below.

$$dx_{si}/dt = r_x d\alpha_{si}/dt \quad (11)$$

$$dy_{si}/dt = r_y d\beta_{si}/dt \quad (12)$$

$$dz_{si}/dt = r_z d\gamma_{si}/dt \quad (13)$$

wherein $(x_{si}, y_{si}, z_{si})$: position information of the measurement target region $p_{si}$ (i=1, 2, 3, . . . ), $(\alpha_{si}, \beta_{si}, \gamma_{si})$: posture information of the measurement target region $p_{si}$ (i=1, 2, 3, . . . ), and $r_x$, $r_y$, $r_z$: radii of rotation of the x-axial, y-axial, and z-axial directions.

When formulae (11) to (13) are solved, results are formulae (14) to (17).

$$l = (r_x^2 + r_y^2 + r_z^2)^{1/2} \quad (14)$$

$$x = x_s - r_x \quad (15)$$

$$y = y_s - r_y \quad (16)$$

$$z = z_s - r_z \quad (17)$$

The length l of the region becoming the calculation target and the coordinates $(x, y, z)$ of the rotation center p as another calculation target can be computed. This calculation method can be applied to calculate measurement target regions such as the length $(l_1+l_2)$ from the shoulder joint $p_0$ to the measurement target region $p_s$ close to the wrist and the coordinates $(x_{p0}, y_{p0}, z_{p0})$ of the shoulder joint $p_0$, the length $l_2$ from the elbow joint $p_1$ to the measurement target region $p_s$ close to the wrist and the coordinates $(x_{p1}, y_{p1}, z_{p1})$ of the elbow joint $p_1$, the length $l_1$ of the upper arm, and the like.

<Process Configuration>

Figure 5:
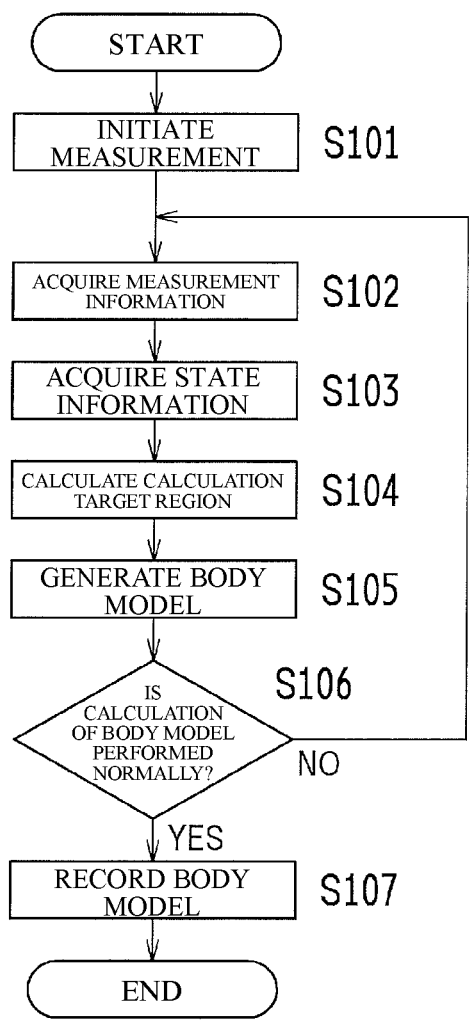
FIG. 5 is a flow chart illustrating an example of a first calculating process of the calculation device set forth herein.

A process of the calculation device 1 that realizes the calculation and is set forth herein will be described. FIG. 5 is a flow chart illustrating an example of a first calculating process of the calculation device 1 set forth herein. The first calculating process is a process of measuring a measurement target region of a worker to acquire measured information, and calculating a calculation target region on the basis of state information calculated from the acquired measured information.

The control unit 10 of the calculation device 1 executes various programs such as the calculation program PG, thereby performing the first calculating process. The control unit 10 of the calculation device 1 causes the wearable device 3 initiate measurement (S101). Step S101 is a process of causing the wearable device 3 to initiate measurement of a physical quantity such as a velocity, an angular velocity, an acceleration, an angular acceleration, a pressure, a magnetism, and the like of the measurement target region, initiating acquisition of the measured information from the wearable device 3 after the measurement of the measurement target region is initiated, and notifying a worker who wears the wearable device 3 to perform a predetermined motion. The notification for notifying performing a predetermined motion refers to output processes such as display of an image, lighting of a display lamp, output of a sound, and the like that are performed due to a motion such as rotation or the like of an arm region such as, for instance, an arm, a forearm, or the like.

After the measurement is initiated by the wearable device 3, the control unit 10 causes the measured information acquisition unit 12 to acquire the measured information two or more times over time (S102). In step S102, the wearable device 3 continues to measure the physical quantity such as the velocity, the angular velocity, the acceleration, the angular acceleration, the pressure, the magnetism, and the like from the worker who performs a predetermined motion such as rotation of his or her arm, rotation of his or her forearm, and the like, for instance, at fixed sampling intervals and outputs the measured information of two or more times which indicates the physical quantity as the measured result to the calculation device 1. The calculation device 1 acquires the measured information output from the wearable device 3.

The control unit 10 causes the state information acquisition unit 10a to obtain and acquire state information such as position information, posture information, and the like of the measurement target region due to a calculation based on the measured information acquired by the measured information acquisition unit 12 (S103). Step S103 is a process of calculating the position information or the position information and the posture information of the measurement target region of a target person as the state information on the basis of the measured information that is acquired by the measured information acquisition unit 12 and is obtained by measuring the measurement target region of the target person. The wearable device 3 may be configured to calculate the state information from the measured information, and the calculation device 1 may cause the state information acquisition unit 10a to acquire the state information output from the wearable device 3 to the calculation device 1 via the measured information acquisition unit 12.

The control unit 10 acquiring the state information causes the body model calculation unit 10b to calculate the calculation target region (S104) to generate a body model on the basis of the calculated result (S105). The calculation of the calculation target region of step S104 is, for instance, calculation in which a length that sets a region from the rotation center in the motion of the worker to the measurement target region is obtained as the calculation target region on the basis of the acquired state information. In the calculation, the length of the calculation target region is calculated by approximately obtaining a circle or a sphere having a length from the rotation center to the calculation target region as a radius thereof using a mathematical method such as a least-squares method on the basis of the state information calculated from a plurality of pieces of measured information acquired over time. A detailed and concrete calculation method and theory are set to refer to the statement about the aforementioned calculation, and descriptions thereof will be omitted here. In step S105, the body model is generated on the basis of the calculated result of the length or the like of the calculation target region.

The control unit 10 determines whether the calculation of the body model is normally performed, for instance, whether abnormality such as an overflow does not occur (S106). In step S106, when it is determined that the calculation of the body model is normally performed (S106: YES), the control unit 10 records the body model, which is the calculated result, on the body model recording unit 11a (S107). In step S106, when it is determined that the calculation of the body model is not normally performed (S106: NO), the control unit 10 returns to step S102 and repeats the processes following the acquisition of the measured information.

In this way, the first calculating process is performed. The first calculating process is a process of calculating the calculation target regions such as the length $(l_1+l_2)$ from the shoulder joint $p_0$ to the measurement target region $p_s$ close to the wrist and the coordinates $(x_{p0}, y_{p0}, z_{p0})$ of the shoulder joint $p_0$, the length $l_2$ from the elbow joint $p_1$ to the measurement target region $p_s$ close to the wrist and the coordinates $(x_{p1}, y_{p1}, z_{p1})$ of the elbow joint $p_1$, the length $l_1$ of the upper arm, and the like in the statement about the aforementioned calculation.

Figure 6:
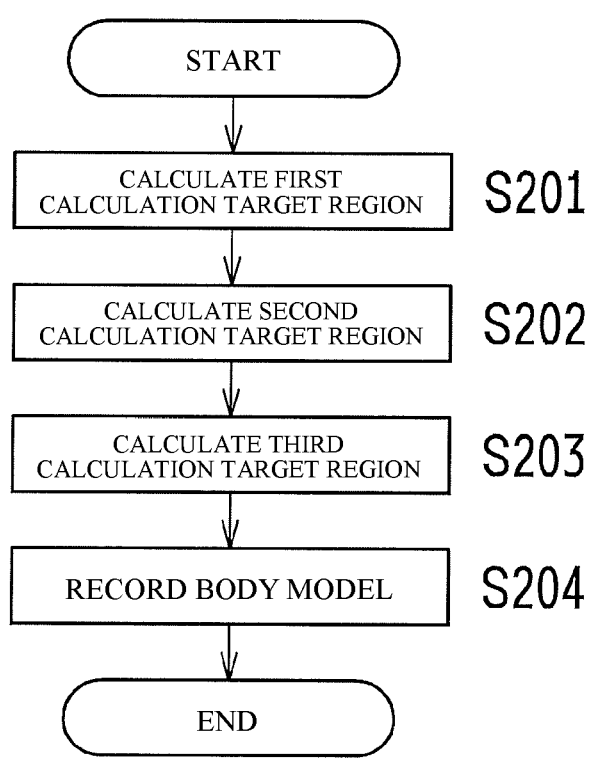
FIG. 6 is a flow chart illustrating an example of a second calculating process of the calculation device set forth herein.

FIG. 6 is a flow chart illustrating an example of a second calculating process of the calculation device 1 set forth herein. The second calculating process is a process of calculating the calculation target region on the basis of the result calculated by the first calculating process.

The control unit 10 of the calculation device 1 executes various programs such as the calculation program PG, thereby performing the second calculating process. The control unit 10 of the calculation device 1 performs a process of calculating a length using a region from a first rotation center to a measurement target region as a first calculation target region (S201). In step S201, the length from the shoulder joint, which is the first rotation center, to the measurement target region is calculated as the first calculation target region, for instance, by the aforementioned first calculating process.

Further, the control unit 10 performs a process of calculating a length using a region from a second rotation center between the first rotation center and the measurement target region to the measurement target region as a second calculation target region (S202). In step S202, the length from the elbow joint, which is the second rotation center, to the measurement target region is calculated as the second calculation target region, for instance, by the aforementioned first calculating process.

The control unit 10 performs a process of calculating a length using a region from the first rotation center to the second rotation center as a third calculation target region on the basis of a difference between the length of the first calculation target region and the length of the second calculation target region (S203). In step S203, for example, the length from the elbow joint to the measurement target region, which is the calculated result of step S202, is subtracted from the length from the shoulder joint to the measurement target region, which is the calculated result of step S201, and thereby a length of the upper arm indicated as a length from the shoulder joint to the elbow joint is calculated as the third calculation target region.

The control unit 10 records the body model on the body model recording unit 11a on the basis of the calculated results of the various calculation target regions obtained by the calculation (S204).

In this way, the second calculating process is performed.

As described above, the calculation device 1 or the like set forth herein can calculate the calculation target usable as the body model only by the worker performing a simple motion such as a rotating motion around his or her shoulder, a rotating motion around his or her elbow, or the like. Since the simple motion can be calculated, information about the body model before work can be acquired. For example, when this information is applied to a technique such as motion sensing, a highly accurate body model can be acquired.

The present invention is not limited to the embodiment described above, and can be performed by other various modes. For this reason, the aforementioned embodiment is merely a simple example, and is not to be restrictively interpreted. The scope of the present invention is defined by the claims, and is not restricted at all by the text of the specification. Further, all alterations or modifications belonging to the equivalent scope of the claims are within the scope of the present invention.

For example, in the above embodiment, the information about the body model is acquired by the rotating motions in which the vicinity of the wrist is set as the measurement target region and the shoulder joint and the elbow joint are set as the centers of rotation is shown, but the present invention is not limited thereto. That is, various regions such as the head, an upper arm, a forearm, the chest, the abdomen, a thigh, a lower leg, and the like can be set as the measurement target regions, and the motions in which various regions such as a radiocarpal joint, a hip joint, a knee joint, a talocrural joint, the waist, the neck, and the like are set as the centers of rotation can be performed.

The invention claimed is:

1. A calculation device that calculates a length of a calculation target region of a human body on the basis of results of measuring a measurement target region of the human body, the calculation device comprising:
a processor configured to:
acquire state information that indicates a position or the position and a state of a posture of the measurement target region of the human body on the basis of measured results;
calculate a length using a region from a rotation center in a motion of the human body to the measurement target region as the calculation target region on the basis of the state information; and
generate a body model relevant to a shape of the human body on the basis of the calculated length for applying to a motion sensing technique, wherein the processor calculates a length using a region from a first rotation center to the measurement target region as a first calculation target region; the processor calculates a length using a region from a second rotation center between the first rotation center and the measurement target region to the measurement target region as a second calculation target region; and the processor calculates a length using a region from the first rotation center to the second rotation center as a third calculation target region on the basis of a difference between the length of the first calculation target region and the length of the second calculation target region.

2. The calculation device according to claim 1, wherein the processor calculates the length of the calculation target region on the basis of the state information by approximately obtaining a circle or a sphere having the length from the rotation center to the calculation target region as a radius.

3. The calculation device according to claim 2, wherein the processor calculates the length of the calculation target region by a least-squares method on the basis of the state information indicating the position of the measurement target region.

4. The calculation device according to claim 3, wherein the rotation center is a joint.

5. The calculation device according to claim 3, further comprising the processor configured to acquire at least one of a velocity, an acceleration, an angular velocity, an angular acceleration, a pressure, and a magnetism, which are the results of measuring the measurement target region of the human body, as measured information,
wherein the processor obtains the state information of the measurement target region of the human body by calculating on the basis of measured information.

6. The calculation device according to claim 2, wherein the rotation center is a joint.

7. The calculation device according to claim 2, further comprising the processor configured to acquire at least one of a velocity, an acceleration, an angular velocity, an angular acceleration, a pressure, and a magnetism, which are the results of measuring the measurement target region of the human body, as measured information,
wherein the processor obtains the state information of the measurement target region of the human body by calculating on the basis of measured information.

8. The calculation device according to claim 1, wherein the rotation center is a joint.

9. The calculation device according to claim 1, further comprising the processor configured to acquire at least one of a velocity, an acceleration, an angular velocity, an angular acceleration, a pressure, and a magnetism, which are the results of measuring the measurement target region of the human body, as measured information,
wherein the processor obtains the state information of the measurement target region of the human body by calculating on the basis of measured information.

10. A calculation method for calculating a length of a calculation target region of a human body on the basis of results of measuring a measurement target region of the human body, the calculation method comprising:
acquiring state information that indicates a position or the position and a state of a posture of the measurement target region of the human body on the basis of the measured results;
calculating a length using a region from a rotation center in a motion of the human body to the measurement target region as the calculation target region on the basis of the state information; and
generating a body model relevant to a shape of the human body on the basis of the calculated length for applying to a motion sensing technique,
wherein the step of calculating the length using the region from the rotation center in the motion of the human body to the measurement target region as the calculation target region on the basis of the state information comprises:
calculating a length using a region from a first rotation center to the measurement target region as a first calculation target region; calculating a length using a region from a second rotation center between the first rotation center and the measurement target region to the measurement target region as a second calculation target region; and calculating a length using a region from the first rotation center to the second rotation center as a third calculation target region on the basis of a difference between the length of the first calculation target region and the length of the second calculation target region.

11. A non-transitory computer-readable recording medium comprising a calculation program that causes a computer to calculate a length of a calculation target region of a human body on the basis of measured information obtained by measuring a measurement target region of the human body, the calculation program causing the computer to perform.
a step of acquiring state information that indicates a position or the position and a state of a posture of the measurement target region of the human body on the basis of the measured results;
a step of calculating a length using a region from a rotation center in a motion of the human body to the measurement target region as the calculation target region on the basis of the acquired state information; and
a step of generating a body model relevant to a shape of the human body on the basis of the calculated length for applying to a motion sensing technique;
wherein the step of calculating the length using the region from the rotation center in the motion of the human body to the measurement target region as the calculation target region on the basis of the acquired state information comprises:
a step of calculating a length using a region from a first rotation center to the measurement target region as a first calculation target region; a step of calculating a length using a region from a second rotation center between the first rotation center and the measurement target region to the measurement target region as a second calculation target region; and a step of calculating a length using a region from the first rotation center to the second rotation center as a third calculation target region on the basis of a difference between the length of the first calculation target region and the length of the second calculation target region.

* * * * *